United States Patent [19]

Plantefeve et al.

[11] Patent Number: 4,839,173

[45] Date of Patent: Jun. 13, 1989

[54] MODIFIED CLAYS, PREPARATION THEREOF AND THERAPEUTICAL COMPOSITIONS CONTAINING THE SAME

[75] Inventors: Jean-Claude Plantefeve, Vernouillet; Michel Rene, Paris, both of France

[73] Assignee: Societe de Conseils de Recherches et d'Applications Scientifiques, France

[21] Appl. No.: 37,236

[22] Filed: Apr. 10, 1987

Related U.S. Application Data

[63] Continuation of Ser. No. 697,331, Feb. 1, 1985, abandoned, which is a continuation-in-part of Ser. No. 483,730, Apr. 11, 1983, abandoned.

[30] Foreign Application Priority Data

Apr. 29, 1982 [GB] United Kingdom ................. 8212448

[51] Int. Cl.$^4$ .............................................. A61K 33/12
[52] U.S. Cl. .................................... 424/683; 424/692
[58] Field of Search ................................ 424/155, 157

[56] References Cited

U.S. PATENT DOCUMENTS

| | | | |
|---|---|---|---|
| 3,041,238 | 6/1962 | Allegrini | 424/154 |
| 3,959,444 | 5/1976 | Yokoi et al. | 423/328 |
| 4,040,974 | 8/1977 | Wright et al. | 252/317 |
| 4,054,537 | 10/1977 | Wright et al. | 252/317 |

*Primary Examiner*—Frederick E. Waddell
*Attorney, Agent, or Firm*—Lucas & Just

[57] ABSTRACT

This invention relates to modified clays comprising a sheet-silicate clay with a plate separation of from 1.5 to 1.6 nm, with a neutralizing power of from 170 to 1200 mEq per 100 g combined with 0.05 to 0.5 part in weight of magnesium hydroxide per part of clay, and acidic addition products of the same. The invention relates also to a preparation process of these clays, consisting in treating at a temperature between 50° C. and about 140° C., possibly under pressure, one part of an appropriate sheet-silicate clay by 0.05 to 0.5 part of magnesium hydroxide for about 3 hours to about 24 hours. The invention relates finally to therapeutic composition of matter comprising as an essential ingredient therein, a sufficient amount of these modified clays.

7 Claims, No Drawings

MODIFIED CLAYS, PREPARATION THEREOF AND THERAPEUTICAL COMPOSITIONS CONTAINING THE SAME

This is a continuation of application Ser. No. 697,331, filed Feb. 1, 1985, now abandoned, which in turn is a continuation-in-part of application Ser. No. 483,730, filed Apr. 11, 1983, now abandoned.

The invention relates to modified clays to be used as active ingredients in medicaments.

Clays are used in therapy, notably to bring about a partial neutralization of too high stomach acidity. They have a moderate neutralizing power, which means the patient has to take several grams of product to obtain the desired effect. Other anti-acid products generally have a too rapid speed of neutralization, and to not provide sufficient permanence for the desired effect. This is the case, for example, with magnesium hydroxide.

The aim is to have slow release of nascent magnesium hydroxide in an anti-acid preparation. The preparation is not a synthetic clay (hectorite or saponite, which are hydrated magnesium silicates) nor a fibrous natural clay mineral such as attapulgite which, to be used in pharmacy, has to be calcined at high temperature and carefully milled. Nor is the preparation a synthetic non-crystalline gel.

The modified clays according to the invention comprise a dioctahedral sheet-silicate clay structure, and have a plate separation of from 1.5 to 1.6 nm (nanometers), a neutralizing power of from 170 to 1200 m equiv (milliequivalents or mEq) per 100 g, and a reduction of the plate separation to from 1.2 to 1.4 nm when heated to 490° C., incorporated into which is from 0.05 to 0.5 part of magnesium hydroxide per part of clay (which means, containing from about 5 to about 33% of magnesium hydroxide).

The modified clays of the present invention are complexes of montmorillonite; this is not only the main raw material but it is regenerated unaltered in use in the stomach. The other ingredient is the hydroxy-magnesium cation with one positive charge ($MgOH^+$) which is formed from brucite, the dihydroxide $Mg(OH)_2$ a neutral mineral species which is formed between parallel layers of montmorillonite. The univalent $Mg(OH)^+$ ion replaces $H^+$ ion and makes hydroxy-Mg-montmorillonite. This $Mg(OH)^+$ ion behaves rather like $Na^+$, causing the clay platelets to disperse, whereas $Mg^{++}$ or $Ca^{++}$ do not do so. The conversion to $MgOH^+$ is made by careful heating (50°–140° C.), and not by calcining, nor is there any hydrothermal alteration of the dioctahedral smectite into some other mineral species.

Because the magnesium hydroxide is incorporated into the clay, the product has a high neutralizing power and a good speed of neutralization but yet retains substantial residual activity. In fact, the clays have been found active for from some tens of minutes to several hours depending on the proportions of starting material used for its preparation and the time and temperature of the reaction. The active ingredient of the medicament combines a excellent neutralizing power into a clay structure in a stable composition so that it is dispensed over a period of time which is longer than for the presently known anti-acids. The combination is a distinct entity; the characteristic X-ray spectrum of the magnesium hydroxide disappears on its formation, and its action is different from that of a mixture in the cold of the same constituents.

The plate separation of the clay is variable as a function of the number of molecules of water, and of the nature and quantity of fixed cations.

The modified clays according to the invention can be prepared from a suitable starting clay, preferably a dioctahedral smectite such as montmorillonite, by treatment in an aqueous phase, preferably under pressure, with magnesium hydroxide added in an appropriate proportion. If the materials used are not dry or perfectly pure (apart from impurities which do not affect the process), the quantities used are adjusted so as to put the quantities of the active ingredients within the necessary ranges. In particular if the clay is in the form of a mud such as can be obtained at the end of the usual purification process, the concentration of the clay in this mud is taken into account. Generally, the clay will be in the form of a mud for the purification of the raw materials if necessary.

This purification is performed as follows:

The mineral is roughly crushed in order to eliminate the stones or hard particles and then suspended in water in a rotatable tube. The aqueous dispersion thus obtained is treated by a chemically pure and strong inorganic acid, under stirring at room temperature, the addition of the acid being made until the pH of the dispersion is between 2 and 3.

Stirring is maintained for about one hour and then the dispersion is diluted and sent to a series of hydrocyclones in which is separated the portion of clays to be used, i.e. the one passing through sieves with a mesh opening of 0.1 mm.

The separated fraction is either used as such or sent to a concentrator for increasing its concentration and dried at a temperature less than 200° C.

A suitable starting clay is a sheet-silicate clay having a plate separation of from 1.2 to 1.5 nm, a neutralizing power above 80 mEq per 100 g and a reduction plate separation to from 0.9 to 1 nm, on heating to 490° C. A dioctahedral montmorillonite clay is preferred.

As to the magnesium hydroxide, the dry material is generally less pure than pastes or suspensions, so it is preferred to use these latter forms of the material and calculate the equivalent quantity which is necessary.

The reaction temperature should be at least 50° C., and depending on the quality of the clay initially used, could be up to 120° C. or even more, the limit being in practice defined by industrial operating conditions and the start of the transformation of the clay. The period of the reaction is a function of the temperature and pressure. The progress of the reaction is tested by the disappearance of the X-ray spectrum lines of magnesium hydroxide (Brucite) on a sample of the mixture.

In the following examples, modified clays according to the invention are prepared in autoclaves from samples each weighing 14 g, containing 2.5 g of clay (smectite, specifically dioctahedral montmorillonite) but various quantities of neutralizing agent, the said 14 g being reached by the addition of water. The quantities of magnesium hydroxide are always given for one part of clay (2.5 g). After placing the sample in the autoclave and closing, the treatment is as follows:

EXAMPLE 1

Magnesium hydroxide paste: 0.606 g corresponding to 0.200 g of pure product (0.08 part). Reaction temperature 90° C. Reaction time 24 hours. Mg(OH)$_2$ rate: 6.45%.

EXAMPLE 2

Magnesium hydroxide paste: 1.819 g corresponding to 0.600 g of pure product (0.24 part). Reaction temperature 90° C. Reaction time 24 hours.

Substantially the same product is obtained by treating the same starting material for 2 hours at 120° C. Mg(OH)$_2$ rate: 19.35%

EXAMPLE 3

Magnesium hydroxide paste: 2.019 g corresponding to 0.606 g of pure product (0.265 parts). Reaction temperature 90° C. Reaction time 24 hours. Mg(OH)$_2$ rate: 21.04%.

EXAMPLE 4

Magnesium hydroxide paste: 2.221 g corresponding to 0.666 g of pure product (0.292 part). Reaction temperature 100° C. Reaction time 24 hours. Mg(OH)$_2$: 22.6%.

EXAMPLE

Magnesium hydroxide paste: 2.273 g corresponding to 0.750 g of pure product (0.30 part). Reaction temperature 120° C. Reaction time 3 hours. Mg(OH)$_2$ content: 23.07%.

EXAMPLE 6

Magnesium hydroxide paste: 2.278 g corresponding to 0.900 g of pure product (0.36 part). Reaction temperature 120° C. Reaction time 4 hours. Mg(OH)$_2$ content: 26.47%.

EXAMPLE 7

Magnesium hydroxide paste: 3.183 g corresponding to 1.050 g of pure product (0.42 part). Reaction temperature 125° C. Reaction time 4 hours. Mg (OH)$_2$ content: 29.58%.

EXAMPLE 8

Magnesium hydroxide paste: 3.638 g corresponding to 1.200 g of pure product (0.48 part). Reaction temperature 142° C. Reaction time 4 hours. Mg(OH)$_2$ content: 32.43%.

After the end of the reaction in each case, the autoclave is cooled and the product recovered in the form of a mud. In order to use the product as such, after washing and drying it is ground to powder. It can then be placed in capsules for oral administration. However, as the product is very basic, it is generally preferred to treat it with carbon dioxide or a therapeutically acceptable acid in order to lower the pH into the range of 7.5 to 9, after which the product is washed and dried, and can be used either in the form of a powder for putting in suspension or pressed to make tablets. Citric, tartaric, phosphoric and silicic acids are therapeutically acceptable and examples of acids which can be used in this way. However, this acid treatment is not compulsory.

Various determinations and experimentations have been conducted to show the interest of the composition of the invention; toxicity has been determined on rats and experimentation on anti-acid activity and coating power have also been reported.

TOXICITY the toxicity of the composition of the invention has been determined on Wistar rats, both male and female, for 5 days at the oral daily dose of 15 g/kg (average weights of the rats: 200 g).

An experimentation has been conducted on 4 batches each of 20 rats:

a first batch of control female rats receiving only physiological serum, in 3 doses of one ml at 8, 12 and 16 hours;

a second batch of 20 female rats receiving 3 times a day, at 8 hours, 12 hours, 16 hours, an oral dose of 5 g/kg of example 5 composition, suspended in 1 ml of water and administered by the intragastric route;

a third batch of control male rats treated as the first batch above, and a fourth batch of male rats treated as the second batch above.

All the animals have been weighed before the experimentation and at the end of the same; the average weight of the female rats increased by 2.67% compared with the control females, whereas the average weights of the male rats decreased by 2.93% compared with the control males.

Accordingly, no significant variation of weight could be noticed during this experimentation. Moreover, no death intervened during this experimentation.

It can be concluded that the composition of the invention, is deprived of any noticeable toxicity.

DETERMINATION OF ANTI-ACID ACTIVITY

The anti-acid activity has been determined by two methods:

(1) In vitro experimentation.

This experimentation was conducted comparatively with a known substance presently on the market and which is a mixture of aluminium and magnesium hydroxides; comparable doses of both compositions have been used, i.e. 2 bags containing 31.2 mEq of neutralizing power for the modified clay according to the invention and 1 dose of the reference compound, containing 41.6 mEq of neutralizing power.

It should be noticed that the reference compounds contained about 25% more of neutralizing power than the modified clay of the invention; however, the comparison has been conducted in that way in order to compare the effectively used therapeutucal doses.

In this experimentation, which was performed according to the technique of Fordtran JS. (Reduction of acidity by diet, antacids, and anticholinergic agents. In Gastro-intestinal disease. Pathophysiology, diagnosis, management. (Sleisenger MH and Fordtran JS, Saunders, Philadelphia) 1973, p. 718–742), each sample of product ws maintained at pH 3 by automatic addition of hydrochloric acid and the graphic representation of the acid demand plotted against the time is recorded continuously and automatically; hydrochloric acid was 0.1 N. From the amounts of acid are determined the used amounts of mEq of each product, the corresponding percentage and the available amounts in mEq at various times.

The results are reported in the following table wherein it appears clearly that:

at about 7 minutes, the reference composition is almost completely neutralized;

the composition of the invention requires about 2 h for being almost completely neutralized.

The compound of the invention has a far longer action and a very progressive pace of neutralization compared to the reference composition.

| Time | | Reference Composition | | | Tested Composition | |
|---|---|---|---|---|---|---|
| | | Used mEq | | Available | Used mEq | | Available |
| h | mm | mEq | % | mEq | mEq | % | mEq |
| 0 | 0 | 5.8 | 14 | 35.8 | 5.9 | 19 | 25.3 |
| 0 | 2 | 16.3 | 39 | 25.3 | — | — | — |
| 0 | 3 | 19.3 | 46 | 22.3 | — | — | — |
| 0 | 5 | 31.6 | 76 | 10.0 | 10.8 | 35 | 20.4 |
| 0 | 6 | 39.5 | 95 | 2.1 | — | — | — |
| 0 | 7 | 40.5 | 97 | 1.1 | — | — | — |
| 0 | 10 | — | — | — | 14.2 | 46 | 17.0 |
| 0 | 20 | — | — | — | 18.8 | 60 | 12.4 |
| 0 | 30 | 41.3 | 99 | 0.3 | 21.8 | 70 | 9.4 |
| 1 | 00 | — | — | — | 26.7 | 86 | 4.5 |
| 1 | 30 | 41.6 | 100 | 0 | 29.0 | 93 | 2.2 |
| 2 | 00 | — | — | — | 30.8 | 99 | 0.4 |
| 2 | 30 | — | — | — | 31.1 | 100 | 0.1 |
| 2 | 45 | — | — | — | 31.2 | 100 | 0 |

(2) In vivo experimentation.

This experimentation was conducted on 12 people and consisted in the intra gastric pH determination at various times after the administration of either the same reference composition or the composition according to the invention.

All the patients received both compositions, one on the first day after a standard meal, and a second one the day after, after the same standard meal; administration was effected in double blind.

In both cases, was determined the time after administration during which the pH value in the stomach was superior or equal to 5 (tested compound gave longer times for 7 patients, eaual times for 3, and shorter time for 2), and superior or equal to 3.5 (tested compound gave longer times for 9 patients, equal times for 2 and shorter time for 1).

The result has, in vivo, the same orientation as in vitro but appears a little less favorable. It should be noticed, however, that the tested composition contained a lower amount of mEq than the reference composition.

The comparative results would surely have been more favorable for the tested composition if same amounts of mEq of both compositions were used.

COATING POWER

The coating power or covering power has been determined on the rats' gastric mucous (male Wistar rats, weight about 250 g).

This experimentation has been conducted comparatively on the composition of the invention, on the starting clay used as raw material for the preparation of the same and with a commercialized reference compound consisting of a gel of magnesium and aluminium hydroxides.

For the composition of the invention, the dose used was 10 ml of the suspension prepared for the composition of Example 4; for the treatment with the clay used as starting material, the suspension has been prepared containing the same amount of clay as the composition of the invention and for the gel of magnesium and aluminium hydroxide, the dose was of 10 ml per kilo which is equivalent to the dose used for the composition of the invention.

The rats were divided into three batches of each eight rats and treated as follows:

The appropriate dose of each product was administered intragastrically to each rat of each batch and ten minutes later, the rats were killed by diethyl ether. The stomachs were taken and opened along the large curve of the same, they were thus placed in recipients containing physiologic serum and smoothly rinsed.

The amount of protective coat is thus expressed by a quote from 0 to 4 in relationship with the coated area and the amount of product (0: no coating at all), average values for these three batches were as follows:

(1) compound of the invention: 2.5
(2) clay used as starting material: 1.9
(3) gel of magnesium and aluminium hydroxide: 0.5.

Accordingly it should be remarked that the commercialized compound is of poor value for the coating of the rats' gastric mucous; the composition of the invention affords it better protection than the clay used as starting material; however, the amount of mineral is the same in both cases.

PRESENTATION—POSOLOGY

The compound according to this invention may be presented in any suitable form for therapeutical administration, such as powder, tablets, gel or suspension, for instance.

In human therapy, unit dose may contain from 1 to 5 g of dry substance.

As examples of suspensions, for instance, may be given:

(1) Composition of the invention

| (Example 3) | 1.900 g |
|---|---|
| Citric acid | 0.008 g |
| Methyl parahydroxybenzoate | 0.008 g |
| Propyl parahydroxybenzoate | 0.004 g |
| Ethyl alcohol at 95° | 0.065 g |
| Saccharose | 1.30 g |
| $CO_2$ (sufficient amount for pH 9 ± 0.5) about | 0.040 g |
| Purified water, sufficient amount for | 9 ml |

This suspension is contained in an individual bag.

(2) Composition of the invention

| (Example 7) | 1.900 g |
|---|---|
| Tartaric acid | 0.070 g |
| Methyl parahydroxybenzoate | 0.010 g |
| Ethyl alcohol at 95° | 0.070 g |
| Saccharose | 1.000 g |
| Purified water, sufficient amount for | 9 ml |

This suspension is contained in an individual bag.

(3) Composition of the invention

| (Example 5) | 1.900 g |
|---|---|
| Methyl parahydroxybenzoate | 0.010 g |
| Menthol | 0.001 g |
| Ethyl alcohol at 95° | 0.065 g |
| Saccharose | 0.050 g |
| $CO_2$ (sufficient amount for pH 8.5 ± 0.5) about | 0.025 g |
| Purified water, sufficient amount for | 8 ml |

This suspension is contained in an individual bag.

As example of powder form, may be given:

(4) Composition of the invention

| (Example 2) | 1.400 g |
|---|---|
| Phosphoric acid | 0.100 g |
| Sorbitol | 0.250 g |

-continued

|  |  |
|---|---|
| Pectine | 0.050 g |
|  | 1.800 g |

This dose is contained in an individual bag.
As example of tablets, may be given:
(5) Composition of the invention

|  |  |
|---|---|
| (Example 6) | 1.400 g |
| Mannitol | 0.250 g |
| Starch | 0.100 g |
| Magnesium stearate | 0.030 g |
| Talc | 0.100 g |
| Silicic acid | 0.020 g |
| Menthol | 0.0005 g |
| Saccharose: sufficient amount for a tablet of | 2 g |

In human therapy, it may be administered from 1 to 12 bags or tablets per diem.

We claim:

1. A modified dioctahedral smectite clay mineral comprising a sheet-silicate clay with a plate separation of from 1.5 to 1.6 nm, with a neutralizing power of from 170 to 1200 mEq per 100 g, with a reduction of the plate separation to from 1.2 to 1.4 nm when heated to 490° C. said sheet-silicate clay having incorporated therein from about 0.05 to 0.5 parts by weight of magnesium hydroxide per part of clay, the incorporation being carried out at a sufficient temperature and for a sufficient period of time so that the characteristic X-ray spectrum of magnesium hydroxide is no longer present.

2. An acidic addition product of the modified clay mineral of claim 1 with carbonic, citric, tartaric, phosphoric and silicic acids.

3. The modified clay mineral of claim 1 wherein the sheet-silicate clay is a dioctahedral montmorillonite clay.

4. A therapeutic composition for use as an antacid comprising, in a pharmaceutically acceptable carrier, an active composition in an amount effective to bring about antacid activity, said active composition comprising a sheet-silicate dioctahedral smectite clay mineral with a plate separation of from about 1.5 to 1.6 nm, with a neutralizing power of from about 170 to 1200 mEq per 100 g, with a reduction of the plate separation to from about 1.2 to 1.4 nm when heated to 490° C. said sheet-silicate clay having incorporated therein from about 0.05 to 0.5 parts by weight of magnesium hydroxide per part of clay, the incorporation being carried out at a sufficient temperature and for a sufficient period of time so that the characteristic X-ray spectrum of magnesium hydroxide is no longer present.

5. The therapeutic composition of claim 4 wherein the active ingredient is an acidic addition product of the said modified sheet-silicate clay with carbonic, citric, tartaric, phosphoric and silicic acids.

6. The therapeutic composition of claim 4 wherein the active ingredient is present in the amount from about 1 to 5 grams per unit dose.

7. The modified clay of claim 4 wherein the sheet-silicate clay is a dioctahedral montmorillonite clay.

* * * * *